US012390630B2

(12) United States Patent
Bettini et al.

(10) Patent No.: US 12,390,630 B2
(45) Date of Patent: Aug. 19, 2025

(54) THREE-WAY CONNECTOR

(71) Applicant: GVS S.P.A., Zola Predosa (IT)

(72) Inventors: Emanuele Bettini, Monte San Pietro (IT); Nicola Scagliarini, Bologna (IT)

(73) Assignee: GVS S.P.A., Zola Predosa (IT)

( * ) Notice: Subject to any disclaimer, the term of this patent is extended or adjusted under 35 U.S.C. 154(b) by 880 days.

(21) Appl. No.: 17/629,658

(22) PCT Filed: Jul. 21, 2020

(86) PCT No.: PCT/IB2020/056822
§ 371 (c)(1),
(2) Date: Jan. 24, 2022

(87) PCT Pub. No.: WO2021/014342
PCT Pub. Date: Jan. 28, 2021

(65) Prior Publication Data
US 2022/0249826 A1 Aug. 11, 2022

(30) Foreign Application Priority Data

Jul. 24, 2019 (IT) .................. 102019000012735

(51) Int. Cl.
*A61M 39/22* (2006.01)
*A61M 39/10* (2006.01)
(52) U.S. Cl.
CPC ........ *A61M 39/223* (2013.01); *A61M 39/105* (2013.01)
(58) Field of Classification Search
CPC .............. A61M 39/223; A61M 39/105; A61M 2039/205; A61M 2039/229
See application file for complete search history.

(56) References Cited

U.S. PATENT DOCUMENTS 5,340,364 A * 8/1994 Ghelli ............. A61B 5/150221
604/32
2018/0296750 A1 10/2018 Larsen et al.

FOREIGN PATENT DOCUMENTS

EP 3108926 A1 12/2016
SE 412945 3/1980
WO 2013017698 A1 2/2013

OTHER PUBLICATIONS

International Search Report and Written Opinion for PCT/IB2020/056822 dated Sep. 17, 2020 (12 pages).

* cited by examiner

*Primary Examiner* — Bradley J Osinski
(74) *Attorney, Agent, or Firm* — Dickinson Wright PLLC

(57) ABSTRACT

A three-way connector (1) including a body (2) with a tubular central part (3) having a first (4) and a second (5) opposite ends, the first end being open and the second end being closed, an internal cavity (6) of the tubular central part (3) communicating with internal ducts (7, 8, 9) of connection portions (10, 11, 12) which project radially from said tubular central part (3), a first (10) and a second (11) intake connection portion being able to receive fluids, at least one of these fluids being infused to a patient by means of the third, output connection portion (12), a tubular valve element (13) with an internal cavity (16) being inserted inside the internal cavity (6) of said central portion (3), and projecting from the first, open end (4) of said tubular central part (3) with a grasping portion (17) thereof with radial arms (17A). The valve element (13) has a shaped tubular body (14) which, selectively can put said connection portions (10, 11, 12) selectively into communication, or close this communication. Transversely inside said internal cavity (16) of the tubular body (14) of the valve element (13) there is present a wall (35) which divides said cavity (16) into two sections (36, 37), a hole (40) in said transverse wall (35) putting these sections of cavity (36, 37) into communication.

5 Claims, 5 Drawing Sheets

THREE-WAY CONNECTOR

RELATED APPLICATIONS

The present disclosure is a national phase application of PCT Application PCT/IB2020/056822, filed on Jul. 21, 2020, which claims priority to Italian Patent Application No. 102019000012735, filed Jul. 24, 2019, the entire contents of each of which are incorporated herein by reference.

FIELD

The subject of the present disclosure is a three-way connector, and preferably a connector for administration of medicine.

BACKGROUND

As is known, a three-way connector (or stopcock) is an auxiliary product which is used in combination with another product during an infusion therapy, for example a syringe. This connector is usually part of a set or kit to administer a fluid intravenously, and which regulates the distribution of said fluid to the vascular system of a patient, such as an administration kit used in applications for administration of drugs, for graduation in said administration, for oncological administrations, and administrations of contrast or nutritional liquids and the like.

A conventional three-way connector comprises a body with a tubular central part, usually with a generally cylindrical form with an internal cavity. This cavity opens at a first end of this body, and is closed at a second end thereof.

The internal cavity of said tubular central part communicates with internal ducts of connection portions in the form of three arms which project radially from the central part of the connector. Two of these connection portions (for intake) can be connected to means for administering fluids; in general, a first portion can be connected to a supply of a physiological solution (for example a bag which is connected by means of a tube to the connector), whereas the second connection portion receives a medical fluid, for example from a syringe or from an infusion line.

The third arm or third connection portion (for output) is on the other hand connected to a tube which carries the fluid to the patient (by means of a catheter or needle). For this purpose, the three-way connector connected to the tube which can transfer the fluid to be infused to the patient is often supported on the patient's body (typically on the arm); in order to permit stable and trouble-free support, the closed end of the central part of the connector is radiated externally, but smooth.

In order to put at least one of the intake connection portions selectively into communication with the output portion, a valve element is provided which is inserted inside the tubular central part of the body of the connector. This valve element is also tubular, cylindrical, and projects from the first end of said tubular central part with a grasping portion thereof which usually has arms projecting radially in order to facilitate gripping of the element.

On the outer surface of the tubular body inserted inside this central part of the connector, the valve element has a hollow which can connect at least one of the intake connection portions selectively to the output portion, or which can intercept and close any communication between the intake and output. This takes place by means of selective rotation of the valve element in the central part of the connector.

The tubular body of the valve element is usually in close contact with the internal wall of the central part of the connector. Thus, in any position of use of the valve element, although at least one of the intake connection portions is connected to a supply of fluid, no drawing of fluid between the tubular body of the valve element and this tubular central part of the connector should persist.

However, we have found that since the three-way connector has various uses, these also include the case of infusions of a fluid with quite high pressures, such as all the possible applications for interventions in cardiology and radiology, angioplasty or various others, which can put at risk said sealing between the valve element and the central part of the connector. In the case of drawing, the fluid administered (which can also be dangerous and toxic for an operator, nurse or doctor who is assisting the patient during the treatment, and/or for the patient himself) could exit from the three-way connector, or, in the case of high pressures, separate the valve element from the body of the connector. This can lead to obvious problems for the people involved.

The same problem can arise if the tubular central part or the tubular body of the valve element has product defects; the possibility is remote, but it is still possible.

EP3108926 describes a connection structure for medical use, and amongst other solutions, it describes a structure of this type in the form of a three-way medical connector. This connector comprises a body provided with three connection portions, i.e. a first portion for a fluid being admitted, a second portion provided with a female element for coupling of the Luer type, and a third portion for output of the fluid. These portions have ducts which end in a tubular hollow central part of this body, which part has a through axial hole, and is open at its opposite ends.

Inside this through-hole there is inserted a tubular valve element provided with hollow opposite parts interrupted by a central baffle or portion in which there is provided a channel which can put the ducts of the three aforementioned connection portions projecting from this tubular central part selectively into communication.

This hollow valve body projects from a first end of the axial through-hole of the central part of the body of the connector; a first hollow part of the tubular valve element opens directly on the exterior of this element, whereas a second hollow part opens on the exterior of the through-hole of the hollow tubular central part of the body of the connector, via the aperture of this through-hole.

EP3108926 deals with the problem of correct coupling of the connection structure with external medical components such as tubes, which coupling is sufficiently sealed by means of appropriate clamping torques of connection elements associated with the connection portions of this structure and at the same time is satisfactorily leak-proof. The European text does not deal with the problem of any leakages of fluid at the hollow central part of the body of the connection structure (and in particular at the three-way valve), which leakages could however no way involve possible excess pressure inside this hollow central part, because it is open at the bottom. Any leakage of fluid between the hollow central part of said body and the tubular valve element placed in it would involve simple exiting of the fluid from the open hole of this hollow central part.

The problem of excess pressure is not even suggested by the European text, because in the solutions which it describes, this problem can not exist. Therefore, this text can not suggest to persons skilled in the art a technical problem which can not arise in any way in the solutions described in the text of the European patent. To consider that the problem of excess pressure could arise for example in the solution described in EP3108926 relative to the three-way connector, and that persons skilled in the art would have faced this problem and solved it in any way is an evaluation which is not based on what is described by the patent text in question, but is based on an ex post facto analysis.

In the three-way connector described in EP3108926, there cannot be creation of any excess pressure at the central part of the body of this valve, and thus in the patent text this possibility of excess pressure is not described.

In addition, because of the presence of the channel inside the tubular valve element, any axial perforation the element may have in order to put its opposite hollow parts into communication could lead to perforation of this channel, with consequent loss of efficiency of the three-way connector.

US2018/296750 describes regulation means for a system for preparing and injecting a fluid in a tomography system with positron emission (PET) and a safety valve to control the flow of this fluid. This valve is shown and described as being a three-way valve with a central body with portions projecting radially for connection to internal ducts for the passage of a fluid.

The central body is hollow, and accommodates valve element with through internal channels, in order to connect the ducts of the projecting portions in a predefined manner. The cavity of the central body is partly closed at one end, where there are present holes in communication with linear hollows which are provided in the internal wall of the central body, and can discharge an excess flow of fluid to the exterior of the valve body, both from one end and the other of said cavity.

Thus, the US text describes means for discharging safely an excess flow of fluid to the exterior of the central body of the valve, said means being hollows in the wall of this connected central body which has apertures in the two end parts, i.e. one end part which partly closes the cavity of this central body, and the other end part being completely open to the external environment, thus always guaranteeing that the function of discharge of the pressure would take place even if the first part were completely closed and did not have apertures.

In addition, the presence of through internal channels in the valve element would prevent axial perforation thereof from occurring.

BRIEF SUMMARY

One objective of the present disclosure is to provide a three-way connector wherein, even in the remote eventuality of drawing of fluid into the cavity of the central part of the connector, there could not be unexpected exiting of this fluid to the exterior of the connector itself, and there could not be disassembly of the parts (connector body and valve element) which constitute the connector as a whole.

A further objective is to provide a three-way connector of the above-described type which is used in a conventional manner, which has low costs, and which can be produced using the conventional techniques for producing three-way connectors according to the prior art.

These objectives and others, which will be apparent to persons skilled in the art, are achieved by a three-way connector according to the main claim.

BRIEF DESCRIPTION OF THE DRAWINGS

For better understanding of the present invention, and purely by way of non-limiting example, the following drawings are appended, in which.

DETAILED DESCRIPTION

Figure 1:
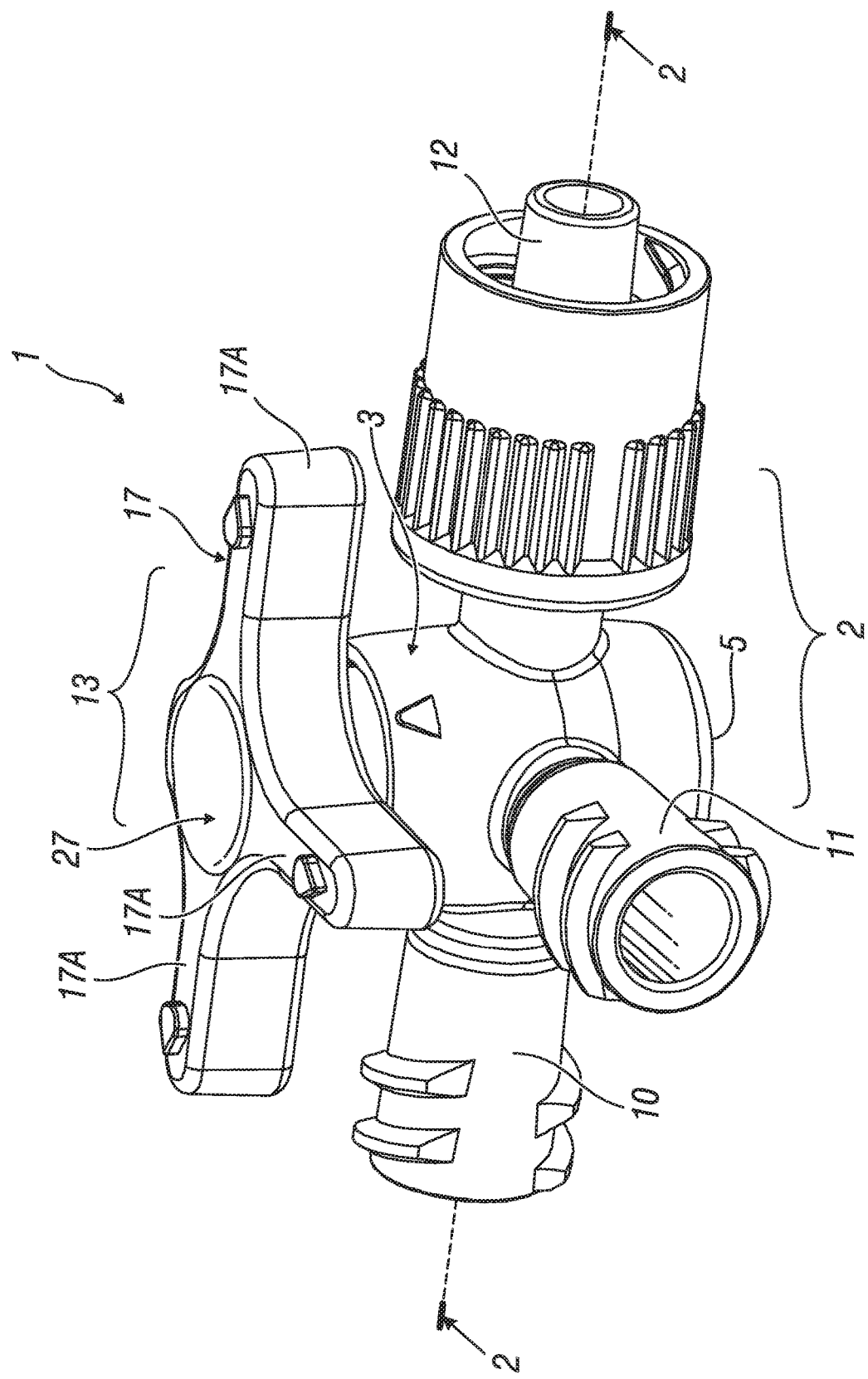
FIG. 1 shows a view in perspective of a three-way connector according to the invention.
Figure 2:
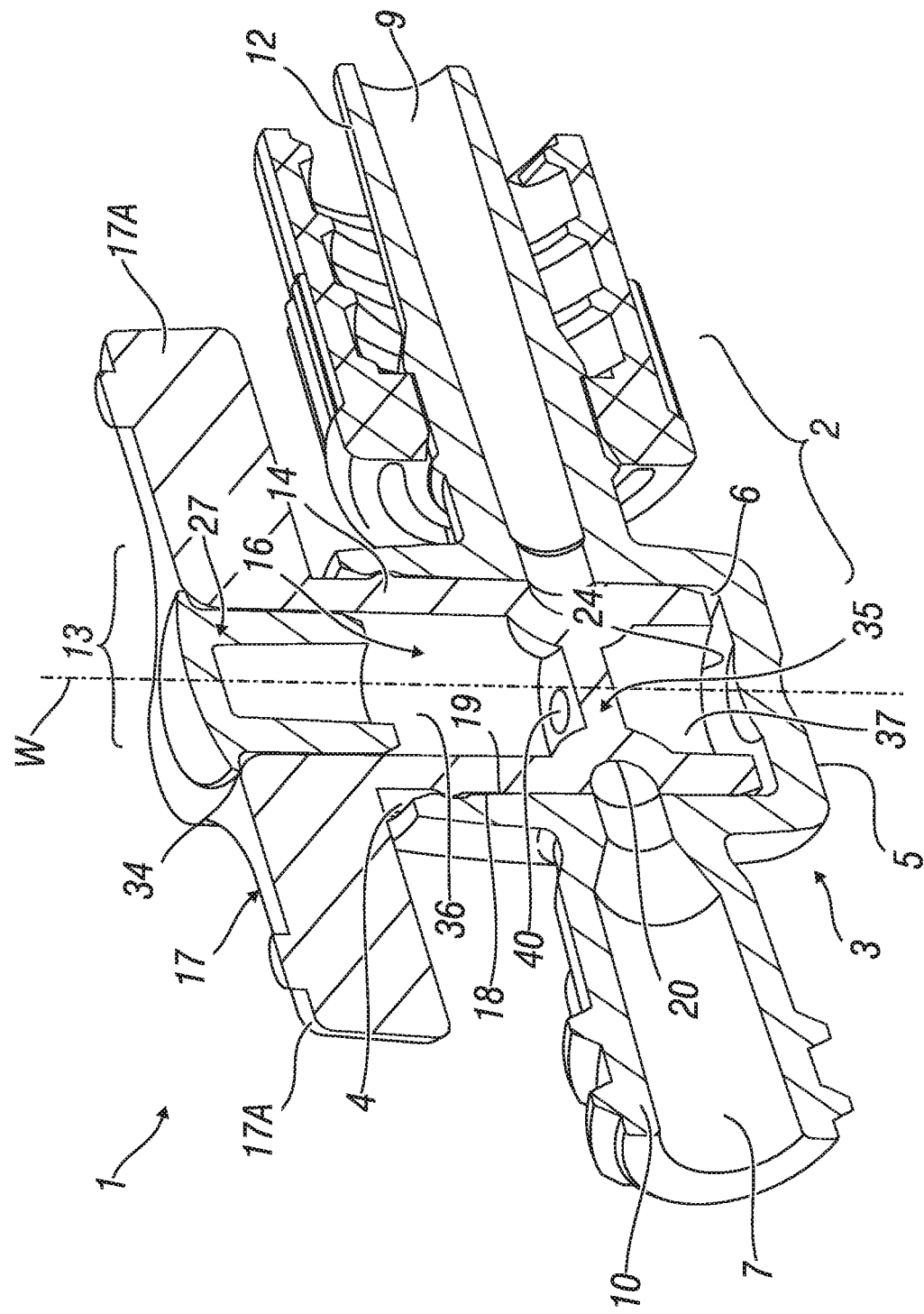
FIG. 2 shows a cross-section according to the line 2-2 in FIG. 1, but from another perspective angle.
Figure 3:
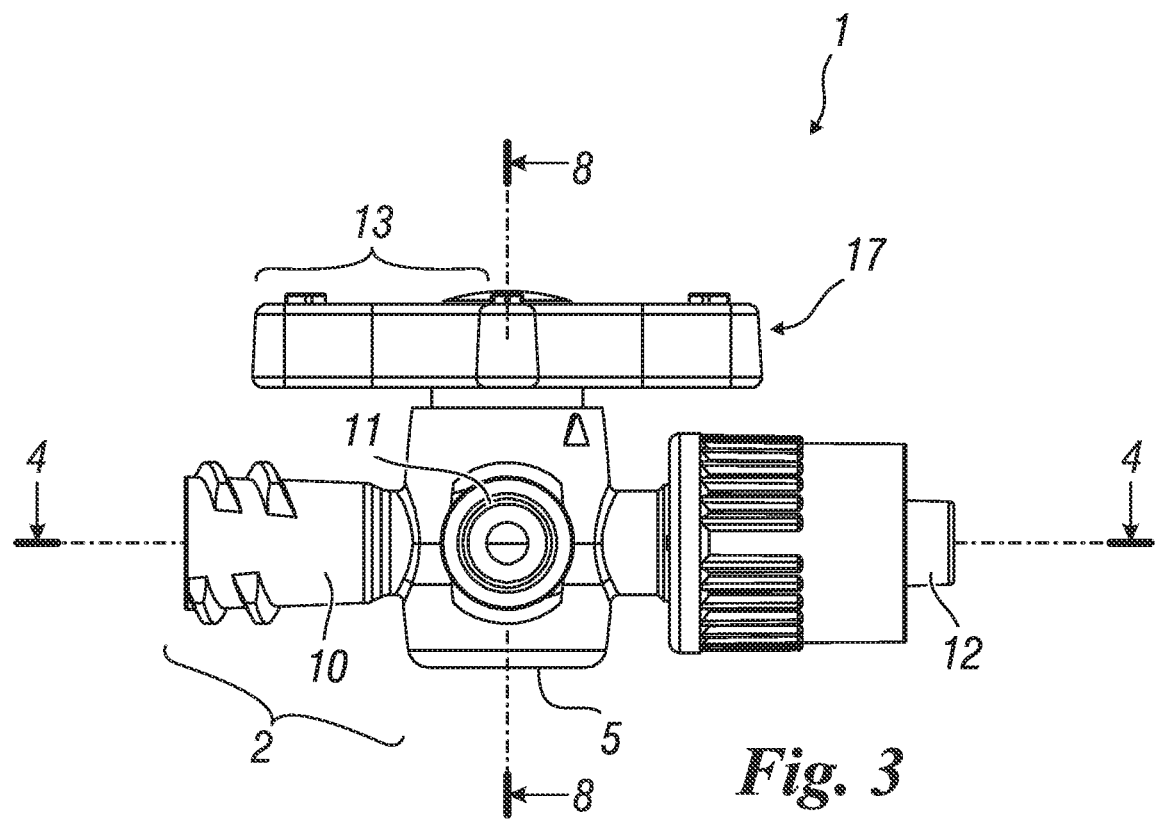
FIG. 3 shows a lateral view of the connector in FIG. 1.
Figure 4:
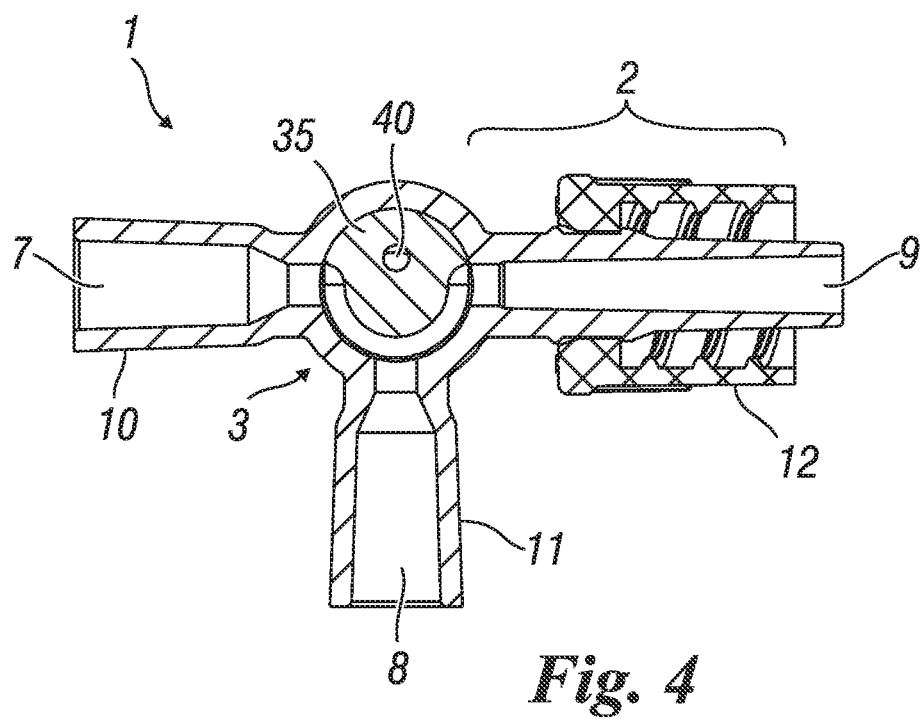
FIG. 4 shows a view in cross-section according to the line 4-4 in FIG. 3.
Figure 5:
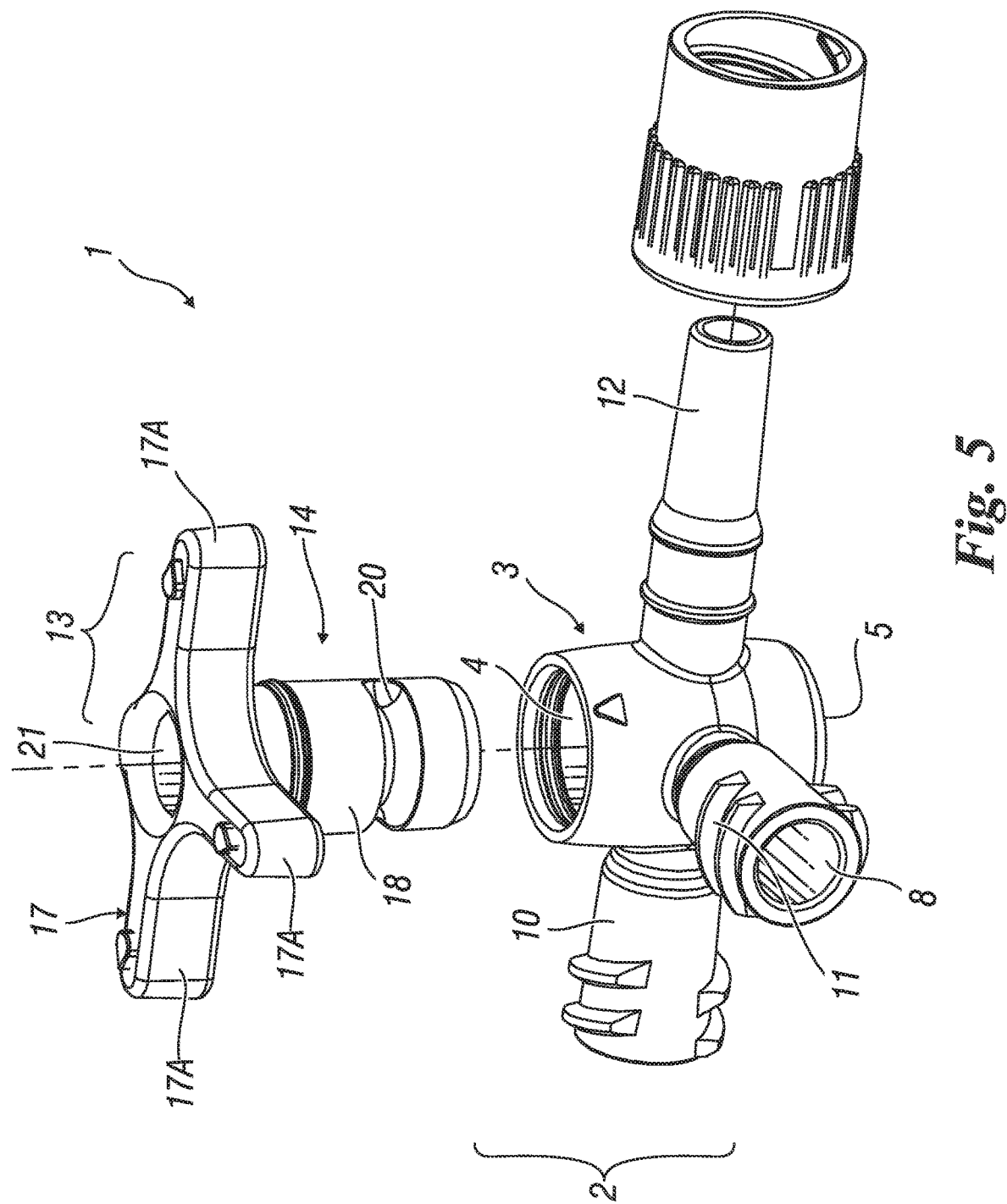
FIG. 5 shows an exploded view in perspective of the connector in FIG. 1.
Figure 6:
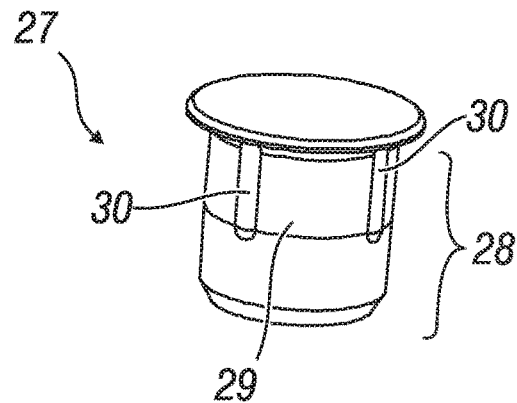
FIG. 6 shows a view in perspective of a part of the connector in FIG. 1.
Figure 7:
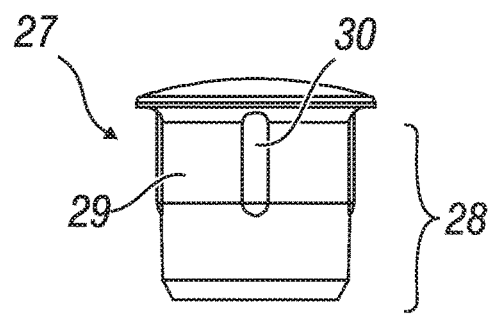
FIG. 7 shows a front view of the part of the connector in FIG. 1 shown in FIG. 6.
Figure 8:
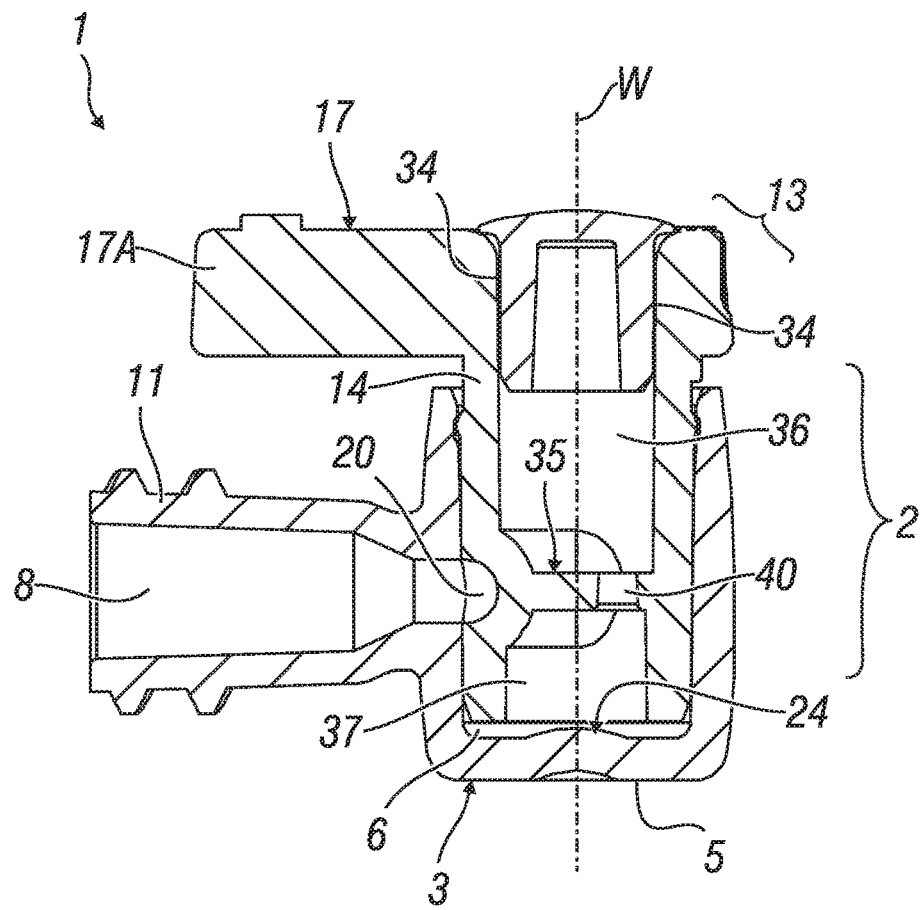
FIG. 8 shows a view in cross-section according to the line 8-8 in FIG. 3.

With reference to said figures, a three-way connector according to the present disclosure is indicated generically as 1. It comprises a body 2 with a tubular central part 3, which is open at a first end 4 and closed at a second end 5. The central part has a cavity 6 to which there are connected ducts 7, 8 and 9, provided respectively inside connection portions 10, 11 and 12 projecting radially from the tubular central part 3. The first and second connection portions (for intake) 10 and 11 can be connected to corresponding supplies of fluids to be administered to a patient in a controlled manner via the three-way connector, by means of the third connection portion (for output of the fluid) 12.

This takes place in a known manner, and will not be described further.

In the cavity 6 of the central part 3 there is inserted a valve element 13 with a tubular body 14 introduced into this cavity of the first end 4 of the central part 3. The tubular body 14 has an internal cavity 16 and an end grasping portion 17 placed on the exterior of the cavity 6 and having radial arms 17A. Inside a surface 18 of this tubular body 14, which can face towards an internal surface 19 of the aforementioned cavity 6, there is provided a hollow 20, the function of which is to put the portions 10, 11 and 12 into selective communication, and permit or prevent administration of fluid to the patient. The body 14 is thus shaped to have said function.

This takes place in a manner which in itself is known to persons skilled in the art, and which will therefore not be described further.

In the embodiment shown in the figures, the grasping portion 17 is perforated centrally by means of a through-hole 21 which defines a first, open end of the internal cavity 16 of the valve element. This cavity 16 is also open at a second end 24 thereof, placed at the front of the second, closed end 5 of the tubular part 3 of the body 2.

In the hole 21, there can be placed a stopper 27 which has a cylindrical body 28 (with any cross-section), having a lateral wall 29 which can be introduced into this hole. However, said wall comprises a plurality of projecting ribs which are longitudinal, helical, or have another position which is not necessarily straight 30, which ribs can space the wall 29 from the edge 33 of the hole 21, and thus create between this edge, said wall and the ribs, channels 34 which are open at their ends. The stopper 27 is usually coloured, and, as is known, by means of its colour it identifies the particular use of a connector, differentiating it from other connectors which are the same, but to be used for other types of infusion.

The cavity 16 of the tubular element 13 has a transverse wall 35, which divides this cavity into two sections, i.e. a first (upper) section 36 which communicates with the hole 21, and a second (lower) section 37 which is closed by the second end 24 of the cavity 16. In said transverse wall 35 there is present a through-hole 40 which puts the two sections 36 and 37 of the cavity 16 into communication. The hole has the function of discharging the pressure which may accumulate in the lower section 37 of the cavity 16, after undesirable drawing of fluid obtained from one of the connection portions (for intake) 10 and 11, which fluid would gather at the second, closed end 5 of the body 2 of the connector 1, and which would pass, gradually filling the lower section 37 of the cavity 16 of the tubular body 14 of the valve element 13.

In the known solutions, where the cavity 16 of the valve element is usually closed, the fluid at the end 5 would give rise to an increase in the pressure of the air blocked between the closure part of the cavity 16 and the end 5 itself, resulting even in bursting effects which would make the valve element 13 becomes separated from the body 2.

If this happens, the fluid which gathers in the lower section 37 of the cavity 16 can pass into the upper section 36 through the hole 40, thus discharging the pressure between the second end 5 of the tubular part 3 of the body 2 and the inside of the cavity 16 (the increase in which pressure could cause the valve element 13 to become detached from the body 2). Thanks to the fact that the fluid can pass through the hole 40 and reach the upper section 36 of the cavity 6 (which is open by means of the through-hole 21, or communicates with the atmosphere via the channels between the wall 29 of the stopper 27, the ribs 30 on said wall and the edge 33 of said hole 21 if the stopper 27 were present therein), and from there exit from said hole 21, the pressure between the end 5 of the body 2 and the aforementioned cavity 16 being always kept low, and thus preventing generation of an axial force capable of disassembling the connector 1 including in a bursting manner, and separating the body 2 from the valve element 13.

The exiting of the fluid from the hole 21 may be noticed by the patient or by a health operator as soon as it takes place, such as to be able to block the infusion operation immediately, and without resulting in more exiting of fluid or separation of parts.

The above-described solution is simple to implement. The hole 40 can be created using known methods in the wall 35, and it can be in-line or off-centred on said wall with reference to a longitudinal axis W of the tubular body 14. If the hole is eccentric, since the wall 35 serves the purpose of withstanding the pressure which persists in the hollow 20, and since the presence of the hole weakens this wall 35, said eccentric position is symmetrical relative to the cross-sectional plane indicated by the line 8-8, such as to minimise the weakening. It will be appreciated that the hole 40 can have any cross-section, or a plurality of holes 40 can be provided in the wall 35.

The invention claimed is:

1. A three-way connector comprising:

a body with a tubular central part having a first end opposite a second end, the first end being open and the second end being closed, an internal cavity of the tubular central part communicating with internal ducts of connection portions which project radially from said tubular central part, a first intake connection portion and a second intake connection portion configured to receive fluids, at least one of the fluids configured to be infused to a patient by way of a third output connection portion, a tubular valve element with an internal cavity inserted inside the internal cavity of said central part and projecting from the open first end of said tubular central part with a grasping portion having radial arms, said valve element having a shaped tubular body which is configured to selectively put said connection portions into communication via a hollow provided inside a surface of said tubular body, or close this communication, wherein, transversely inside said internal cavity of the tubular body of the valve element, there is present a wall which divides said cavity into two sections, a hole in said transverse wall putting these sections of cavity into communication.

2. Three-way connector according to claim 1, wherein said hole in the transverse wall is placed alternatively on a longitudinal axis of said tubular body of the valve element, or in a position which is eccentric relative to this axis.

3. Three-way connector according to claim 1, wherein the two sections of the internal cavity of the tubular body of the valve element includes a first section and a second section, the first section located in an area of the grasping portion, the second section being open at the second end of the tubular central part of the body of the connector.

4. Three-way connector according to claim 3, wherein the first section of the cavity communicates with a through-hole provided in the grasping portion of the valve element.

5. Three-way connector according to claim 4, wherein, in said through-hole there is disposed a stopper having a cylindrical body with a lateral wall inserted in said through-hole, longitudinally and on the exterior of this lateral wall a plurality of projecting ribs being provided which can contact directly an edge of the hole, and space the lateral wall of the stopper from this edge, a plurality of channels thus being provided between said lateral wall, said edge and said ribs, said channels being open at their opposite ends such as to communicate with the internal cavity of the valve element and with the exterior of the element.

* * * * *